United States Patent
Schmidt et al.

(10) Patent No.: US 7,429,733 B2
(45) Date of Patent: Sep. 30, 2008

(54) METHOD AND SAMPLE FOR RADIATION MICROSCOPY INCLUDING A PARTICLE BEAM CHANNEL FORMED IN THE SAMPLE SOURCE

(75) Inventors: Michael B. Schmidt, Gresham, OR (US); Tracy D. Myers, Clackamas, OR (US)

(73) Assignee: LSI Corporation, Milpitas, CA (US)

( * ) Notice: Subject to any disclaimer, the term of this patent is extended or adjusted under 35 U.S.C. 154(b) by 331 days.

(21) Appl. No.: 11/323,405

(22) Filed: Dec. 29, 2005

(65) Prior Publication Data
US 2007/0152151 A1  Jul. 5, 2007

(51) Int. Cl.
*H01J 37/28* (2006.01)

(52) U.S. Cl. .................. 250/311; 250/306; 250/307; 250/308; 250/492.21; 250/491.1; 216/39; 438/460

(58) Field of Classification Search ......... 250/306–308, 250/310, 311, 491.1, 492.1, 492.2, 492.21, 250/492.3; 216/39; 438/460
See application file for complete search history.

(56) References Cited

U.S. PATENT DOCUMENTS

| | | | | |
|---|---|---|---|---|
| 5,656,811 A | * | 8/1997 | Itoh et al. ................ | 250/309 |
| 5,977,543 A | * | 11/1999 | Ihn et al. ................ | 250/311 |
| 6,188,068 B1 | * | 2/2001 | Shaapur et al. .......... | 250/307 |
| 6,194,720 B1 | * | 2/2001 | Li et al. .................. | 250/311 |
| 6,362,474 B1 | * | 3/2002 | Okihara ................... | 250/304 |
| 6,426,500 B1 | * | 7/2002 | Chang et al. ............. | 250/307 |
| 6,576,894 B1 | * | 6/2003 | Doong .................... | 250/282 |
| 6,621,081 B2 | * | 9/2003 | Moran .................... | 250/307 |
| 6,646,263 B2 | * | 11/2003 | Kwakman et al. ........ | 250/310 |
| 2004/0016888 A1 | * | 1/2004 | Haraguchi ............ | 250/440.11 |
| 2005/0064610 A1 | * | 3/2005 | Bruley et al. ............. | 438/14 |

* cited by examiner

*Primary Examiner*—Jack I. Berman
*Assistant Examiner*—Michael J Logie
(74) *Attorney, Agent, or Firm*—Eric James Whitesell (57) ABSTRACT

A method and sample for radiation microscopy include a sample source that includes an area of interest, an outer side of a sample formed in the sample source adjacent to the area of interest, an inner side of the sample formed inside the sample source wherein at least a portion of the area of interest is included between the inner side of the sample and the outer side, and a particle beam channel formed inside the sample source for conducting a particle beam to or from the inner side of the sample.

14 Claims, 14 Drawing Sheets

METHOD AND SAMPLE FOR RADIATION MICROSCOPY INCLUDING A PARTICLE BEAM CHANNEL FORMED IN THE SAMPLE SOURCE

BACKGROUND OF THE INVENTION

1. Field of the Invention

The present invention is directed to the design and manufacture of integrated circuits. More specifically, but without limitation thereto, the present invention is directed to a method of examining the microstructure of a semiconductor material used in an integrated circuit die.

2. Description of Related Art

In the design and manufacture of integrated circuits, transmission electron microscopy (TEM) is used to bombard a thin sample, typically less than 200 nanometers thick, with a highly focused beam of electrons. The electron signal transmitted through the sample is magnified and observed, for example, through electron diffraction or direct electron imaging techniques to generate a sample image. Electron diffraction patterns are used to determine the crystallographic structure of the sample, while direct electron images yield information about the microstructure of the sample and defects that may be present in the microstructure. In scanning transmission electron microscopy (STEM), the electron beam is raster scanned across the sample.

SUMMARY OF THE INVENTION

A method and sample for radiation microscopy is described that includes a particle beam channel formed in the sample source.

In one embodiment, an apparatus includes:
a sample source that includes an area of interest;
an outer side of a sample formed in the sample source adjacent to the area of interest;
an inner side of the sample formed inside the sample source wherein at least a portion of the area of interest is included between the inner side of the sample and the outer side; and a particle beam channel formed inside the sample source for conducting a particle beam to or from the inner side of the sample.

In another embodiment, a method includes steps of:
providing a sample source that includes an area of interest;
forming an outer side of a sample in the sample source adjacent to the area of interest;
forming an inner side of the sample inside the sample source wherein the sample includes at least a portion of the area of interest between the inner side of the sample and the outer side; and
forming a particle beam channel inside the sample source for conducting a particle beam to or from the inner side of the sample.

BRIEF DESCRIPTION OF THE DRAWINGS

The above and other aspects, features and. advantages will become more apparent from the description in conjunction with the following drawings presented by way of example and not limitation, wherein like references indicate similar elements throughout the several views of the drawings, and wherein.

Elements in the figures are illustrated for simplicity and clarity and have not necessarily been drawn to scale. For example, the dimensions, sizing, and/or relative placement of some of the elements in the figures may be exaggerated relative to other elements to clarify distinctive features of the illustrated embodiments. Also, common but well-understood elements that may be useful or necessary in a commercially feasible embodiment are often not depicted in order to facilitate a less obstructed view of the illustrated embodiments.

DESCRIPTION OF THE ILLUSTRATED EMBODIMENTS

The following description is not to be taken in a limiting sense, rather for the purpose of describing by specific examples the general principles that are incorporated into the illustrated embodiments. For example, certain actions or steps may be described or depicted in a specific order to be performed. However, practitioners of the art will understand that the specific order is only given by way of example and that the specific order does not exclude performing the described steps in another order to achieve substantially the same result. Also, the terms and expressions used in the description have the ordinary meanings accorded to such terms and expressions in the corresponding respective areas of inquiry and study except where other meanings have been specifically set forth herein.

Figure 1:
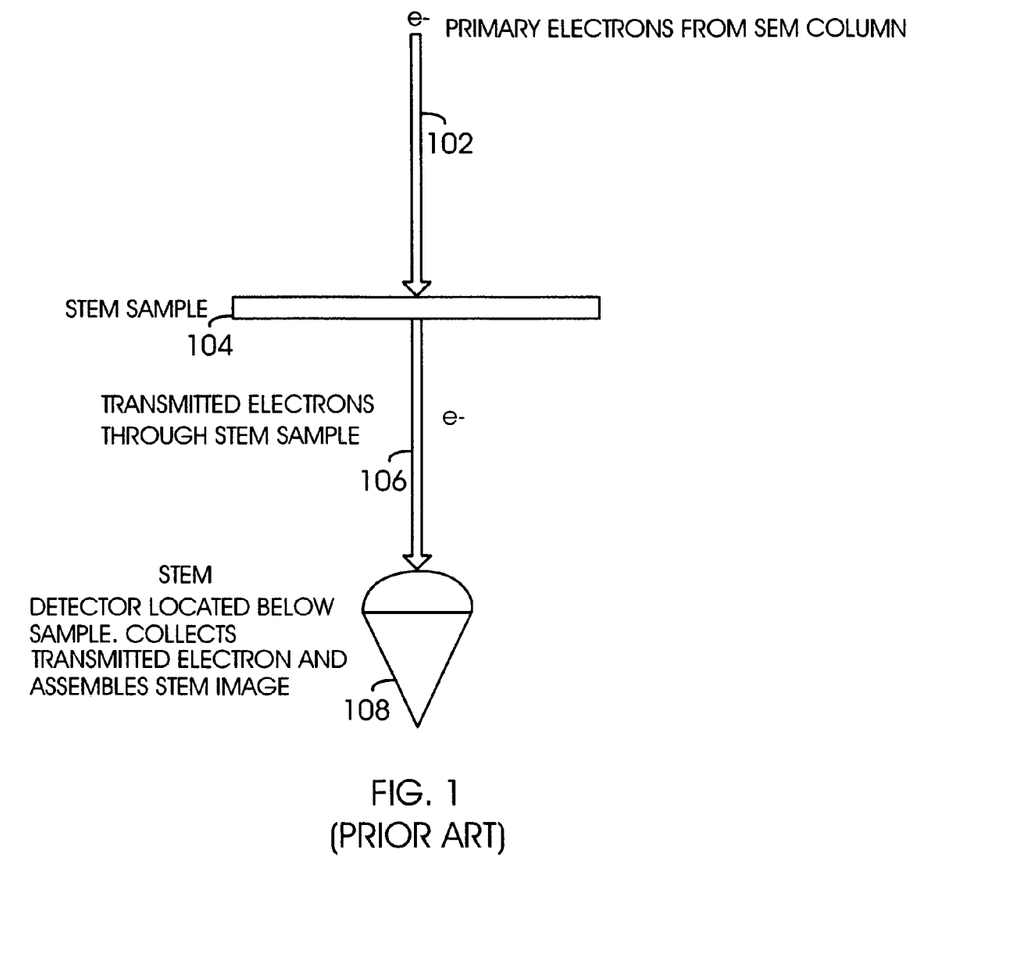
FIG. 1 illustrates a typical scanning transmission electron microscopy (STEM) configuration of the prior art for imaging a sample from a beam of transmitted electrons.

FIG. 1 illustrates a typical scanning transmission electron microscopy (STEM) configuration of the prior art for imaging a beam of transmitted electrons. Shown in FIG. 1 are a beam of primary electrons 102, a STEM sample 104, a beam of transmitted electrons 106, and a transmitted electron detector 108.

In FIG. 1, the beam of primary electrons 102 is received from a scanning electron microscope column or a dual-beam focused ion beam (FIB) generator (not shown) and scanned across the STEM sample 104. The scanning electron microscope column includes electronic lenses that focus the beam of electrons into a small volume on the STEM sample 104. The electrons that pass through the STEM sample 104 form the beam of transmitted electrons 106 below the STEM sample 104. The transmitted electron detector 108 receives the beam of transmitted electrons 106 from the STEM sample 104 and the position of the beam of primary electrons 102 from the scanning electron microscope column and assembles an image of the STEM sample 104 as a plot of the intensity of the transmitted electrons 106 vs. the X-Y coordinate of the beam of primary electrons 102 on the STEM sample 104.

Figure 2:
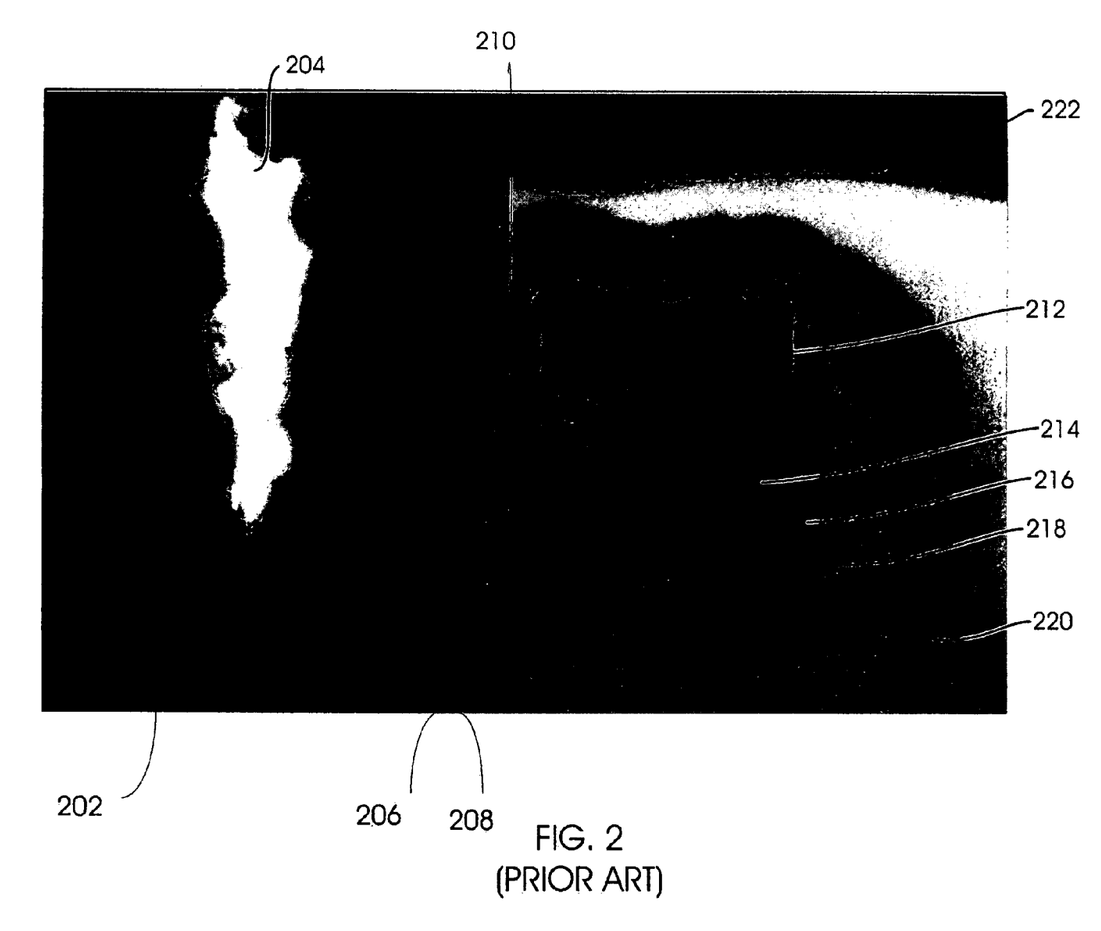
FIG. 2 illustrates a sample image of a polysilicon gate of a transistor assembled by the STEM detector of FIG. 1.

FIG. 2 illustrates a sample image 200 of a polysilicon gate of a transistor assembled by the STEM detector of FIG. 1. Shown in FIG. 2 are a tungsten contact 202, a void 204, a titanium nitride layer 206, a pure titanium layer 208, a structural defect 210, a cobalt salicide layer 212, a polycrystalline silicon layer 214, a silicon oxide layer 216, a silicon nitride sidewall spacer 218, a silicon nitride etch stop 220, and a platinum layer 222.

In FIG. 2, the tungsten contact 202 includes the void 204, a common artifact resulting from the tungsten deposition. Adjacent to the tungsten contact 202 is the titanium nitride layer 206 and the pure titanium layer 208. The structural defect 210 is believed to be a "stringer" of titanium from the pure titanium layer 208 that extends to the cobalt salicide layer 212. The silicon oxide layer 216 separates the polycrystalline silicon layer 214 from the silicon nitride sidewall spacer 218, and outside the silicon nitride sidewall spacer 218 is the silicon nitride etch stop 220. The platinum layer 222 is a conductive, protective coating used to preserve the polysilicon gate sample.

Figure 3:
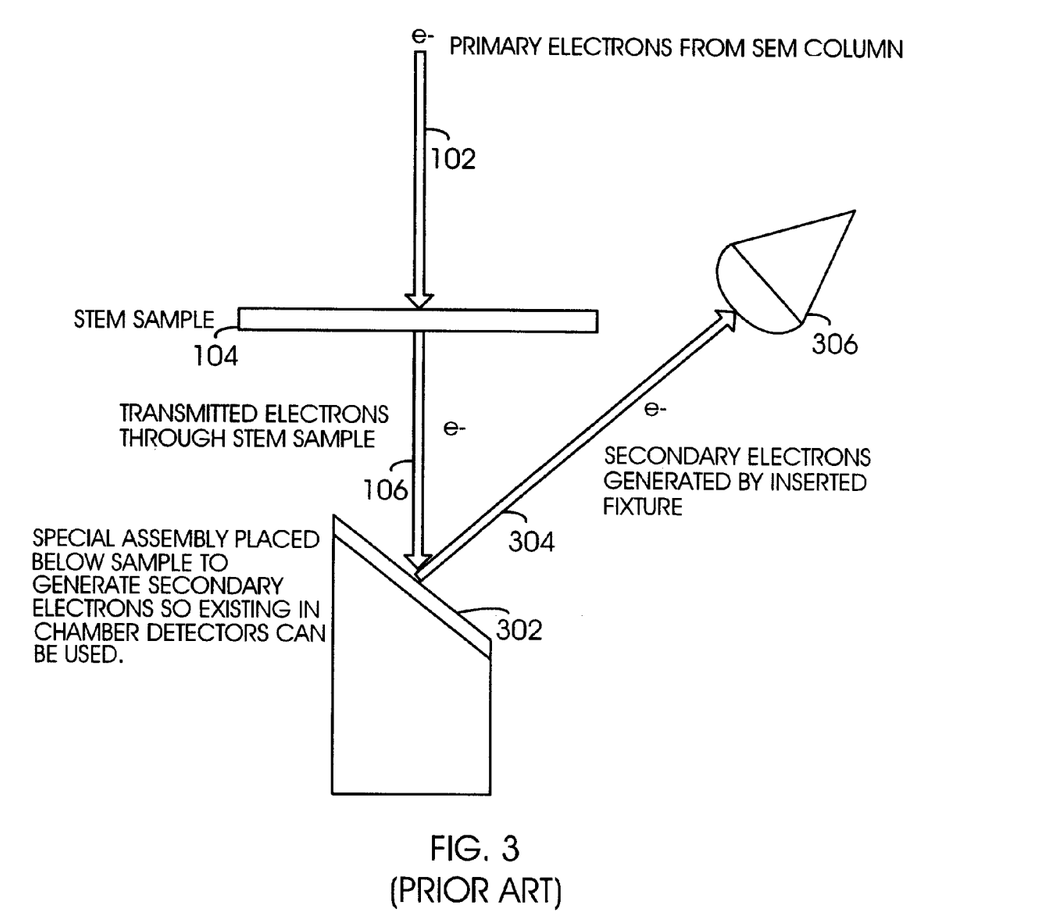
FIG. 3 illustrates a typical scanning transmission electron microscopy (STEM) configuration of the prior art for imaging a beam of secondary electrons.

FIG. 3 illustrates a typical scanning transmission electron microscopy (STEM) configuration of the prior art for imaging a beam of secondary electrons. Shown in FIG. 3 are a beam of primary electrons 102, a STEM sample 104, a beam of transmitted electrons 106, a secondary electron generator 302, a beam of secondary electrons 304, and an in-chamber secondary electron detector 306.

In FIG. 3, the beam of primary electrons 102 is received from a scanning electron microscope column or a dual-beam focused ion beam (FIB) generator (not shown) and scanned across the STEM sample 104 to generate the beam of transmitted electrons 106 below the STEM sample 104. The beam of transmitted electrons 106 from the STEM sample 104 raises the energy of the electrons inside the secondary electron generator 302 to generate the beam of secondary electrons 304 toward the in-chamber secondary electron detector 306. Because the in-chamber secondary electron detector 306 is typically included in a scanning electron microscope, the secondary electron generator 302 may be used by inserting the secondary electron generator 302 instead of the transmitted electron detector 108 in FIG. 1.

The in-chamber secondary electron detector 306 assembles an image of the STEM sample 104 as a plot of the intensity of the beam of secondary electrons 304 and the position of the beam of primary electrons 102 in the same manner as in FIG. 1 to generate the sample image of FIG. 2.

The arrangements of FIG. 1 and FIG. 3 each require the preparation of the STEM sample 104. In previous methods for preparing samples for transmission electron microscopy (TEM) and scanning transmission electron microscopy (STEM), the samples are typically as small as 15 microns wide, 100 nanometers thick, and 10 microns deep. While sufficient for some applications, such small sample sizes may be extremely fragile and may require costly equipment for sample preparation and handling. In addition, any special handling equipment required for handling the sample inside a test chamber may result in increased cost for testing the sample.

The arrangement of FIG. 3 also requires the addition of the secondary electron generator 302 to use the in-chamber secondary electron detector 306. Accordingly, a method for preparing STEM samples is desired that avoids special handling tools and the secondary electron generator 302 for use with the in-chamber secondary electron detector 306. A method of preparing a STEM sample that overcomes the disadvantages above and provides other advantages is described as follows. Although a STEM sample is used to illustrate the following examples, the method and sample described below may be used to practice other embodiments to suit various applications within the scope of the appended claims.

In one embodiment, a scanning transmission electron microscopy sample includes:
  a sample source that includes an area of interest;
  an outer side of a sample formed in the sample source adjacent to the area of interest;
  an inner side of the sample formed inside the sample source wherein at least a portion of the area of interest is included between the inner side of the sample and the outer side; and
  a particle beam channel formed inside the sample source for conducting a particle beam to or from the inner side of the sample.

Figure 4:
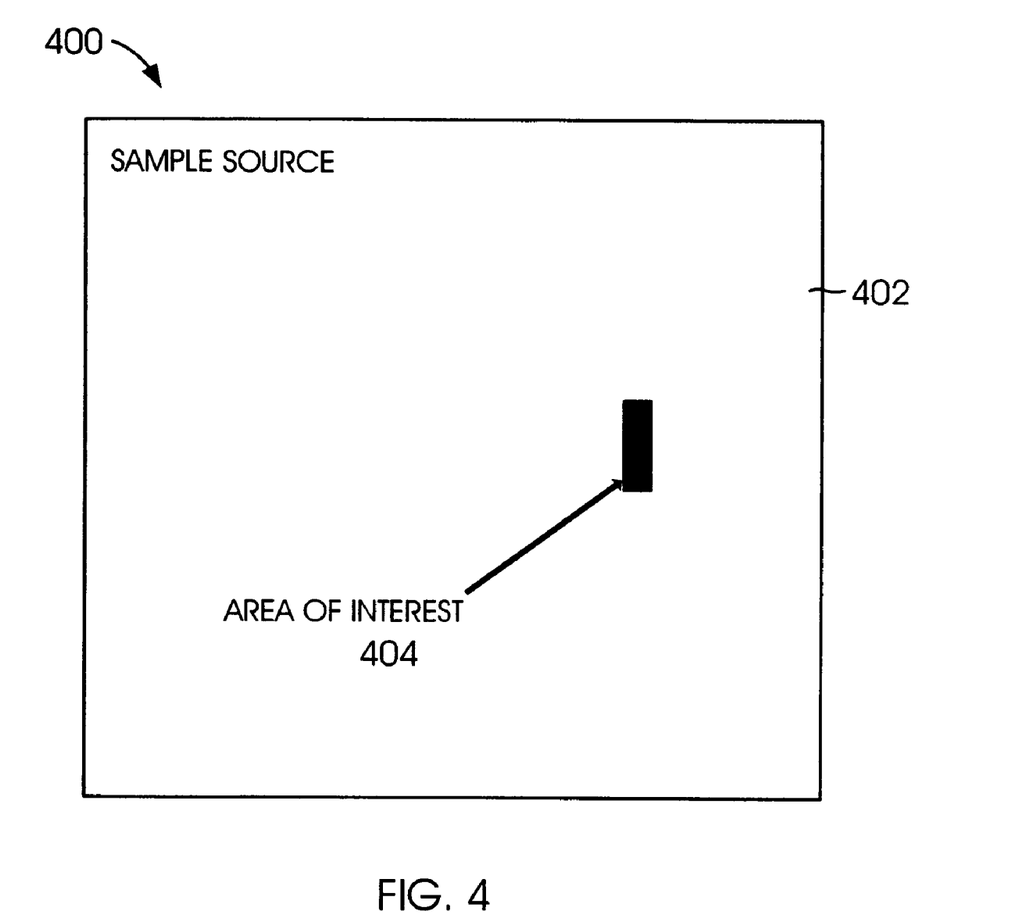
FIG. 4 illustrates a top view of a sample source that includes an area of interest.

FIG. 4 illustrates a top view 400 of a sample source 402 that includes an area of interest 404. The sample source 402 may be, for example, a semiconductor wafer used in the manufacture of integrated circuit die. The area of interest 404 may be, for example, an area on the sample source 402 that is known to enclose a via, a metal contact, an oxide layer, a polysilicon layer, or a specific location of a defect found during wafer testing or in-line inspection. A sample that includes the area of interest 404 is to be prepared from the sample source 402 to generate a magnified image of the microstructure of the area of interest illustrated in FIG. 2.

Figure 5:
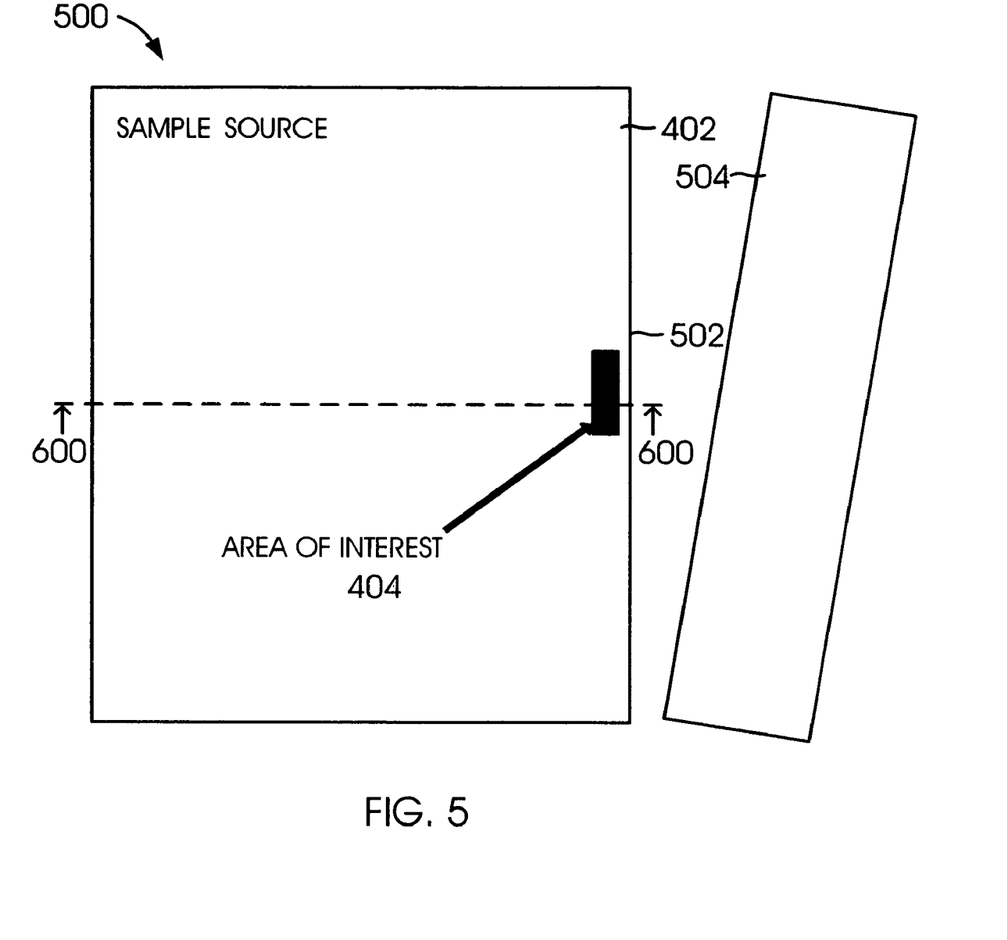
FIG. 5 illustrates a top view of the sample source of FIG. 4 after forming the outer side of a sample adjacent to the area of interest.

FIG. 5 illustrates a top view 500 of the sample source of FIG. 4 after forming the outer side of a sample adjacent to the area of interest. Shown in FIG. 5 are a sample source 402, an area of interest 404, an outer side 502, a portion 504 that has been removed from the sample source 400, and a reference line for a sectional view 600.

In FIG. 5, the portion 504 may be removed from the sample source 402, for example, by a micro-cleaver to form the outer side 502 of the sample adjacent to the area of interest 404. The micro-cleaving step may be performed, for example, by manually scribing a line on the sample source 402 with a diamond scribe near the area of interest, typically from zero to about 20 microns from the area of interest 404, and striking the portion 504 to break the portion 504 away from the sample source 402 along the scribe line. In other embodiments, the outer side may be formed further than 20 microns from the area of interest 404. Commercially available micro-cleavers include a translation table for automatically positioning the sample source 402 precisely under the diamond scribe. Alternatively, the micro-cleaver may be a dicing saw, a laser, a focused ion beam (FIB), or other device suitable for removing the portion 504.

Figure 6:
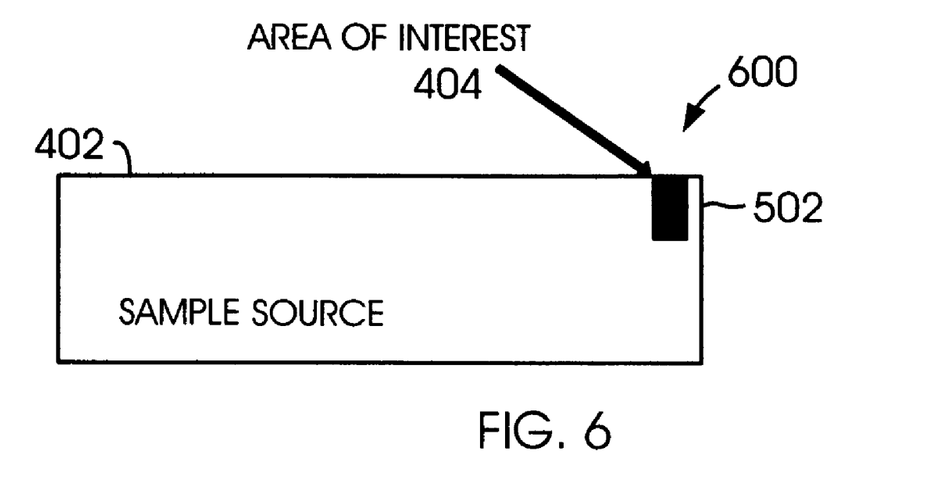
FIG. 6 illustrates a side view of the sample source of FIG. 5 after forming the outer side.

FIG. 6 illustrates a side view 600 of the sample source of FIG. 5 after forming the outer side. Shown in FIG. 6 are a sample source 402, an area of interest 404, and an outer side 502.

In FIG. 6, the depth of the sample source 402 is preferably greater than the depth of the area of interest 404 to provide bulk support for handling the sample and for integrating a particle beam channel in the sample source 402. For example, a typical semiconductor wafer used in the manufacture of integrated circuits has a thickness in the range of 500 microns to 700 microns, while the depth of the area of interest 404 may be only 10 microns.

Figure 7:
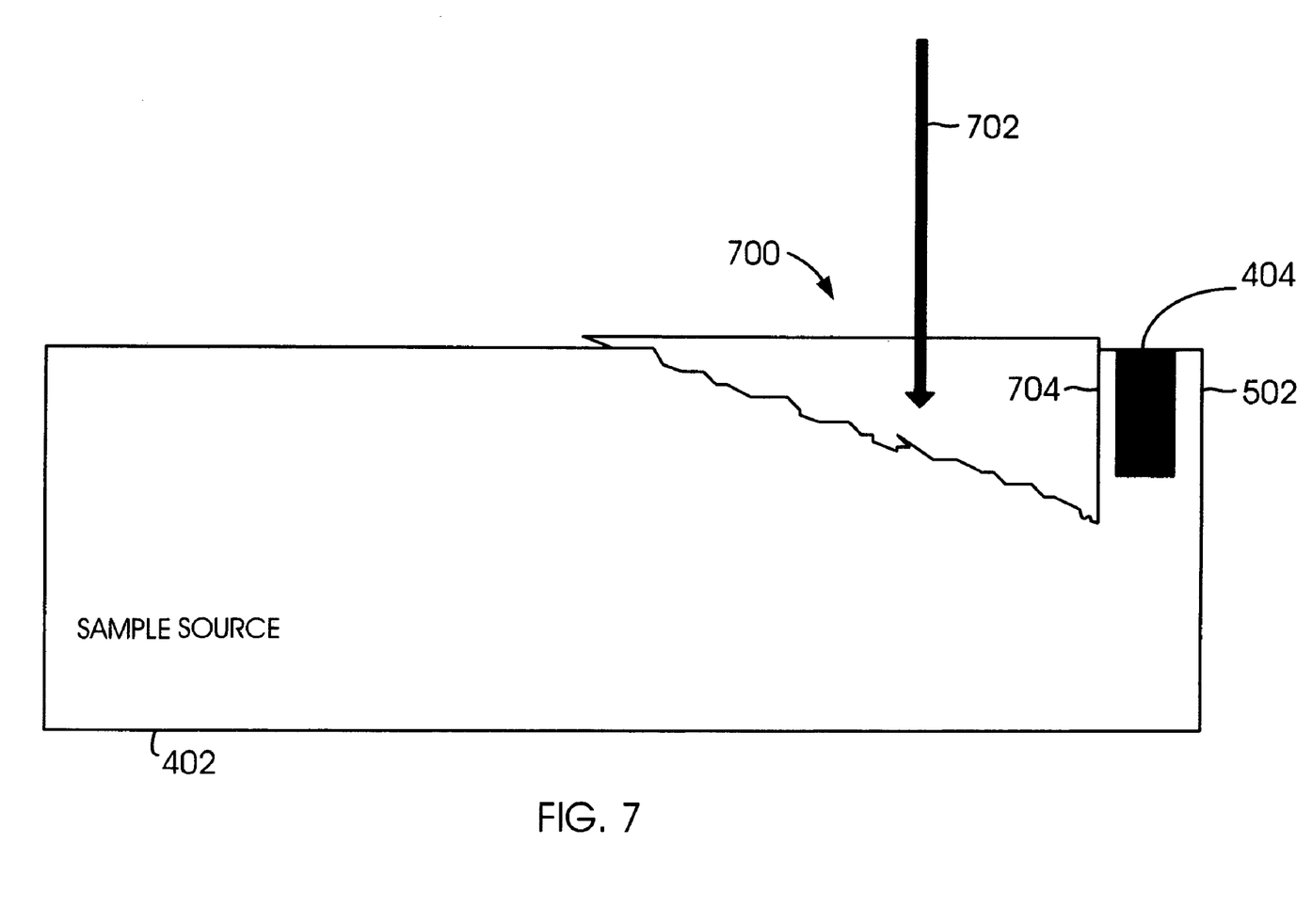
FIG. 7 illustrates a side view of the sample source of FIG. 5 after forming the inner side of the sample.

FIG. 7 illustrates a side view 700 of the sample source of FIG. 6 after forming the inner side of the sample. Shown in FIG. 7 are a sample source 402, an area of interest 404, an outer side 502, a focused ion beam (FIB) 702, and an inner side of the sample 704.

In FIG. 7, the inner side of the sample 704 may be formed, for example, by varying the intensity of the focused ion beam (FIB) 702 aimed perpendicularly to the top surface of the sample source 402 to remove material from the sample source 402, forming a channel terminated by the inner side of the sample 704. The intensity of the focused ion beam (FIB) 702 is reduced while being scanned in a direction away from the area of interest 404 to form the angled channel in the sample source 402 that extends from a depth below the area of interest 404 at the inner side of the sample 704 to the top of the sample source 402.

Figure 8:
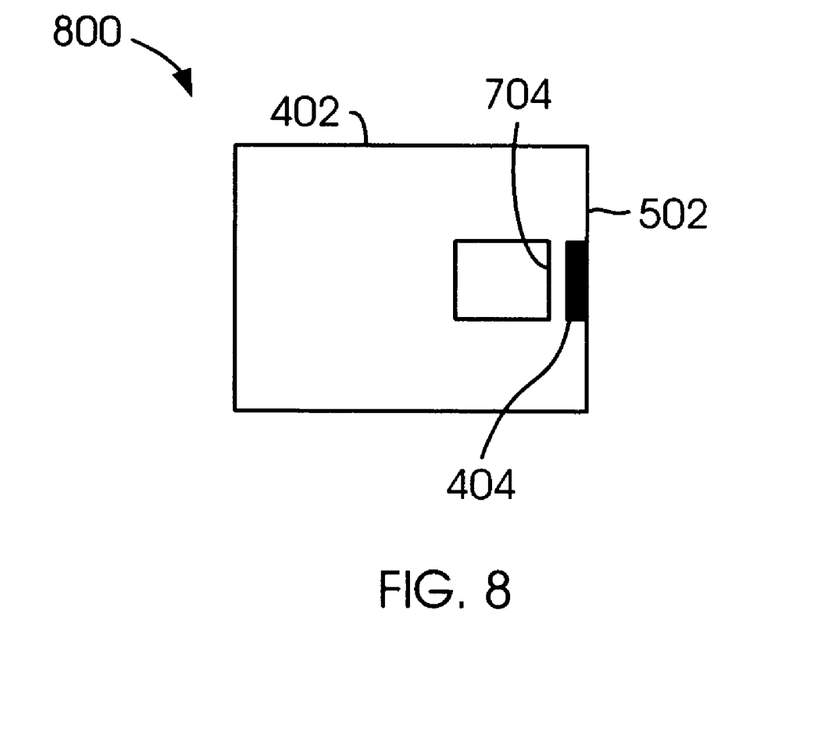
FIG. 8 illustrates a top view of the sample source of FIG. 7 after forming the inner side of the sample.

FIG. 8 illustrates a top view 800 of the sample source of FIG. 7 after forming the inner side of the sample. Shown in FIG. 8 are a sample source 402, an area of interest 404, an outer side 502, and an inner side of the sample 704.

In FIG. 8, the width of the inner side of the sample 704 is preferably the same as the width of the area of interest 404.

Figure 9:
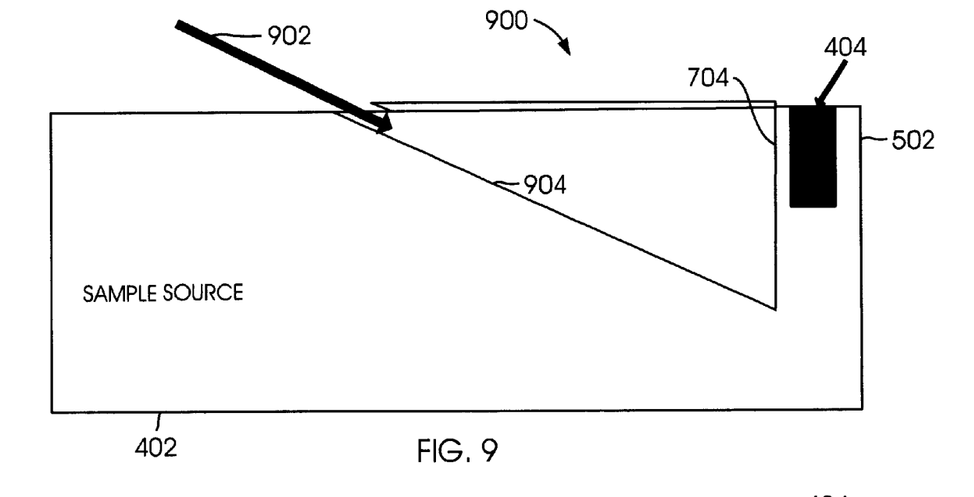
FIG. 9 illustrates a side view of the sample source in FIG. 7 after forming the particle beam channel.

FIG. 9 illustrates a side view 900 of the sample source in FIG. 7 after forming the particle beam channel. Shown in FIG. 9 are a sample source 402, an area of interest 404, an outer side 502, an inner side of the sample 704, a focused ion beam (FIB) 902, and a particle beam channel 904.

In FIG. 9, the angular surface of the particle beam channel 904 is planed, for example, by the same focused ion beam (FIB) 702 used to form the inner side of the sample 704, except that the aim of the focused ion beam (FIB) 902 is parallel to the angular surface of the particle beam channel 904. The angle of the particle beam channel 904 is selected, for example, to generate secondary electrons from a beam of transmitted electrons conducted by the particle beam channel 904 from the sample.

Figure 10:
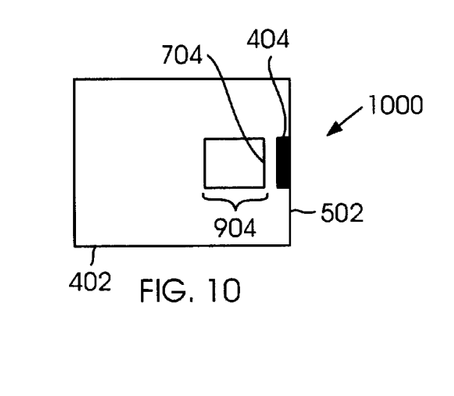
FIG. 10 illustrates a top view of the sample source of FIG. 9 after planing the particle beam channel.

FIG. 10 illustrates a top view 1000 of the sample source of FIG. 9 after planing the particle beam channel. Shown in FIG. 10 are a sample source 402, an area of interest 404, an outer side 502, an inner side of the sample 704, a focused ion beam (FIB) 902, and a planed particle beam channel 904.

In FIG. 10, the width of the planed particle beam channel 904 is preferably the same as the width of the area of interest 402.

Figure 11:
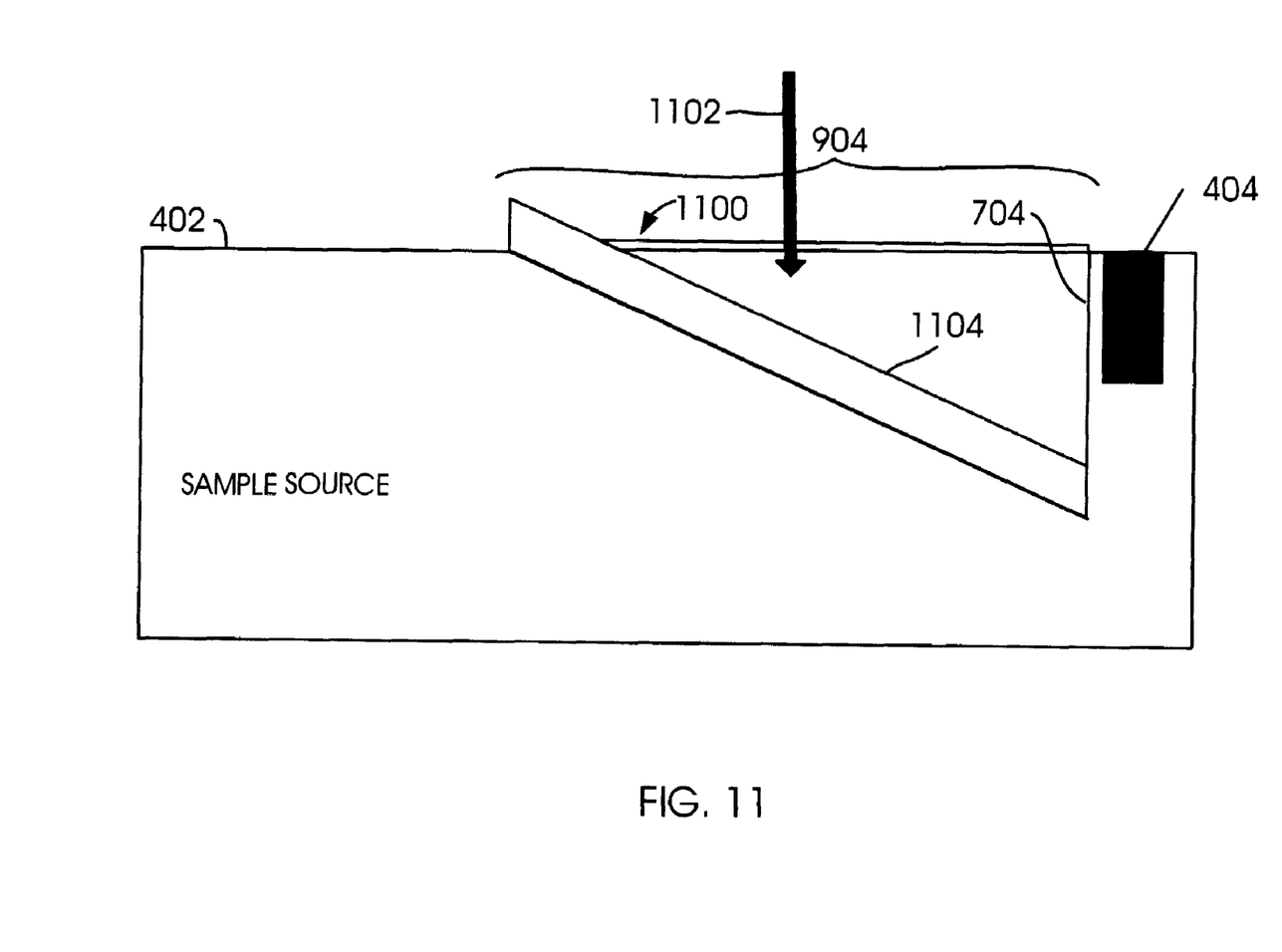
FIG. 11 illustrates a side view of the sample source of FIG. 9 after coating the particle beam channel.

FIG. 11 illustrates a side view 1100 of the sample source of FIG. 9 after coating the particle beam channel. Shown in FIG. 11 are a sample source 402, an area of interest 404, an outer side 502, an inner side of the sample 704, a particle beam channel 904, a deposition ion beam 1102, and a particle beam channel coating 1104.

In FIG. 11, the deposition ion beam 1102 is used to deposit the particle beam channel coating 1104 on the planed surface of the particle beam channel 904, preferably avoiding accidental deposition on the inner side of the sample 704. The particle beam channel coating 1104 may be, for example, a material having a high atomic number such as platinum or gold for generating secondary electrons. In other embodiments, the particle beam channel coating 1104 may be a reflective material such as silver, for example, for reflecting a laser beam to the inner side of the sample 704. Also, other methods may be used for coating the planed surface of the particle beam channel 904 according to well-known techniques to practice various embodiments within the scope of the appended claims.

Figure 12:
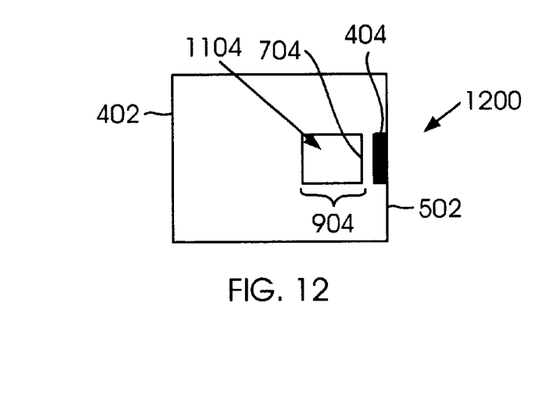
FIG. 12 illustrates a top view of the source sample of FIG. 9 after coating the particle beam channel.

FIG. 12 illustrates a top view 1200 of the sample source of FIG. 11 after coating the particle beam channel. Shown in FIG. 12 are a sample source 402, an area of interest 404, an outer side 502, an inner side of the sample 704, a particle beam channel 904, and a particle beam channel coating 1104.

In FIG. 12, the particle beam channel coating 1104 preferably extends from the top of the sample source 400 sufficiently close to the inner side of the sample 704 to avoid undesired masking of the particle beam directed along the particle beam channel 904 and the inner side of the sample 704.

Figure 13:
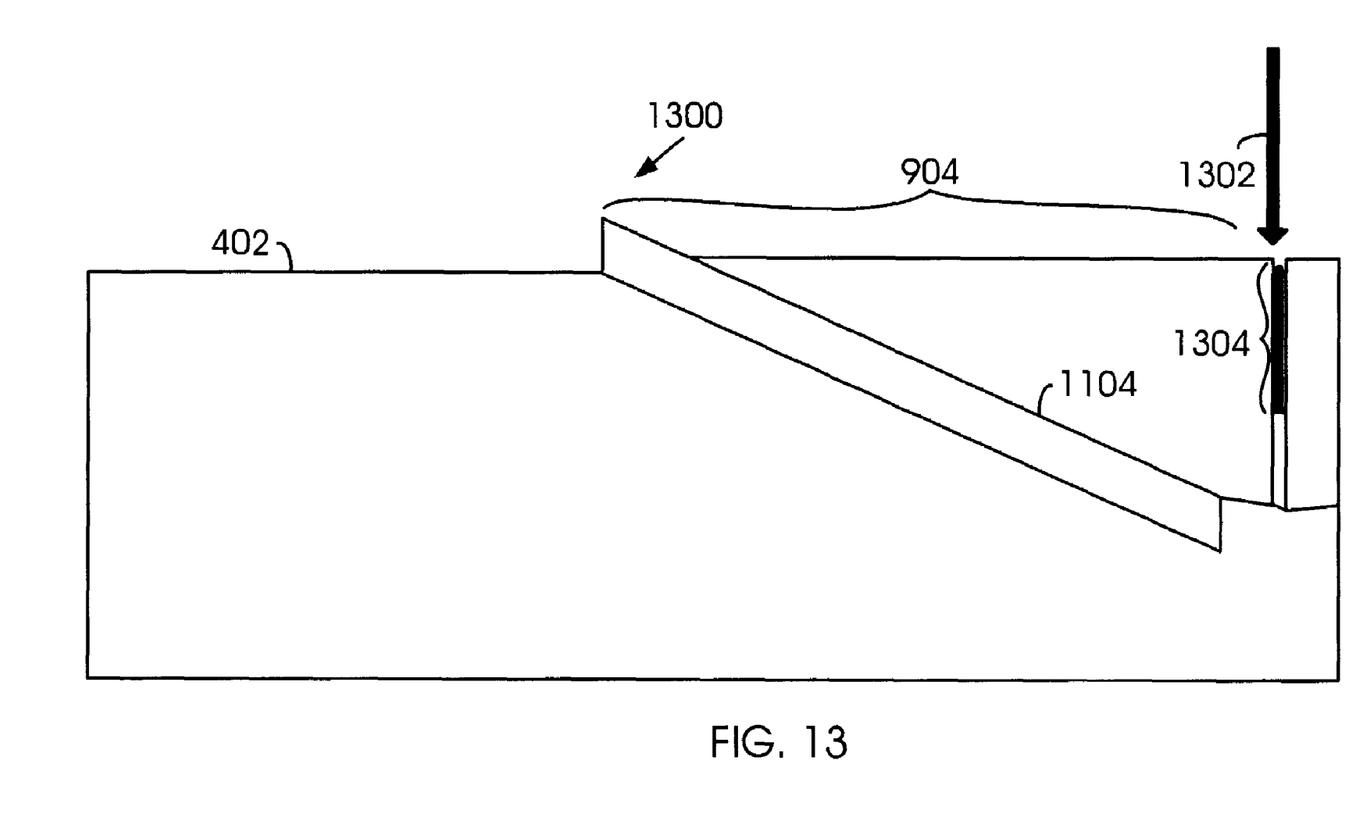
FIG. 13 illustrates a side view of the sample source of FIG. 11 after thinning the sample.

FIG. 13 illustrates a side view 1300 of the sample source of FIG. 11 after thinning the sample. Shown in FIG. 13 are a sample source 402, a particle beam channel 904, a particle beam channel coating 1104, a thinning beam 1302, and a sample 1304.

In FIG. 13, the area of interest 404 in FIG. 11 is thinned on the inner side of the sample 704 and on the outer side 502 to form the sample 1304. The thickness of the sample 1304 is selected, for example, so that the sample 1304 is semi-transparent to a beam of primary electrons. The thinning beam 1302 used to thin the sample 1304 may be, for example, the same focused ion beam (FIB) 702 used to form the inner side of the sample 704. The thinned sample includes a portion of the area of interest 402 having a desired thickness.

Figures 14, 15:
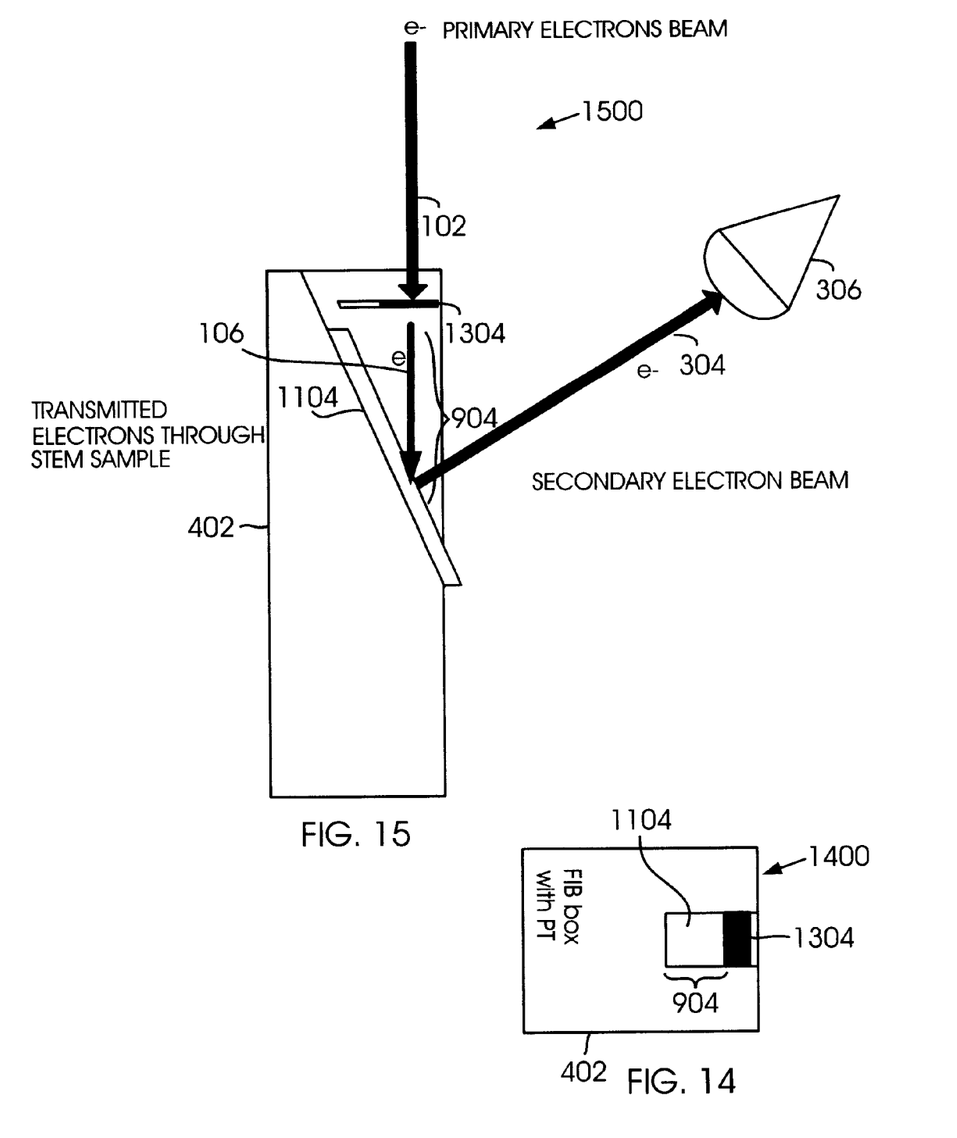
FIG. 14 illustrates a top view of the sample source of FIG. 13 after thinning the sample.
FIG. 15 illustrates a side view of a scanning transmission electron microscopy (STEM) configuration using the sample of FIG. 14.

FIG. 14 illustrates a top view 1400 of the sample source of FIG. 13 after thinning the sample. Shown in FIG. 14 are a sample source 402, a particle beam channel 904, a particle beam channel coating 1104, and a sample 1304.

In FIG. 14, the sample 1304 may have the typical thickness used in samples of the prior art that generally require handling by special tools called micro-manipulators. However, the sample 1304 is supported inside the much larger bulk of the sample source 402, obviating the need for micro-manipulators. The mechanical support provided for the sample 1304 inside the sample source 402 advantageously reduces the risk of damage to the sample 1304 by tools commonly used for manual and automatic wafer handling.

FIG. 15 illustrates a side view 1500 of a scanning transmission electron microscopy (STEM) configuration using the sample of FIG. 14. Shown in FIG. 15 are a beam of primary electrons 102, a beam of transmitted electrons 106, a beam of secondary electrons 304, an in-chamber secondary electron detector 306, a sample source 402, a particle beam channel 904, a particle beam channel coating 1104, and a sample 1304.

In FIG. 15, the beam of primary electrons 102 passes through the sample 1304 to generate the beam of transmitted electrons 106. The beam of transmitted electrons 106 is conducted by the particle beam channel 904 to the particle beam channel coating 1104, generating the beam of secondary electrons 304. The in-chamber secondary electron detector 306 detects the beam of secondary electrons 304 and assembles the image of the sample in the same manner as described above with regard to FIG. 3. The particle beam channel 904 is preferably formed sufficiently deep and wide to assemble the entire image of the sample over the area of interest.

In alternative embodiments, the particle beam channel coating 1104 may be used to reflect a beam of photons or other atomic and sub-atomic particles as follows.

Figure 16:
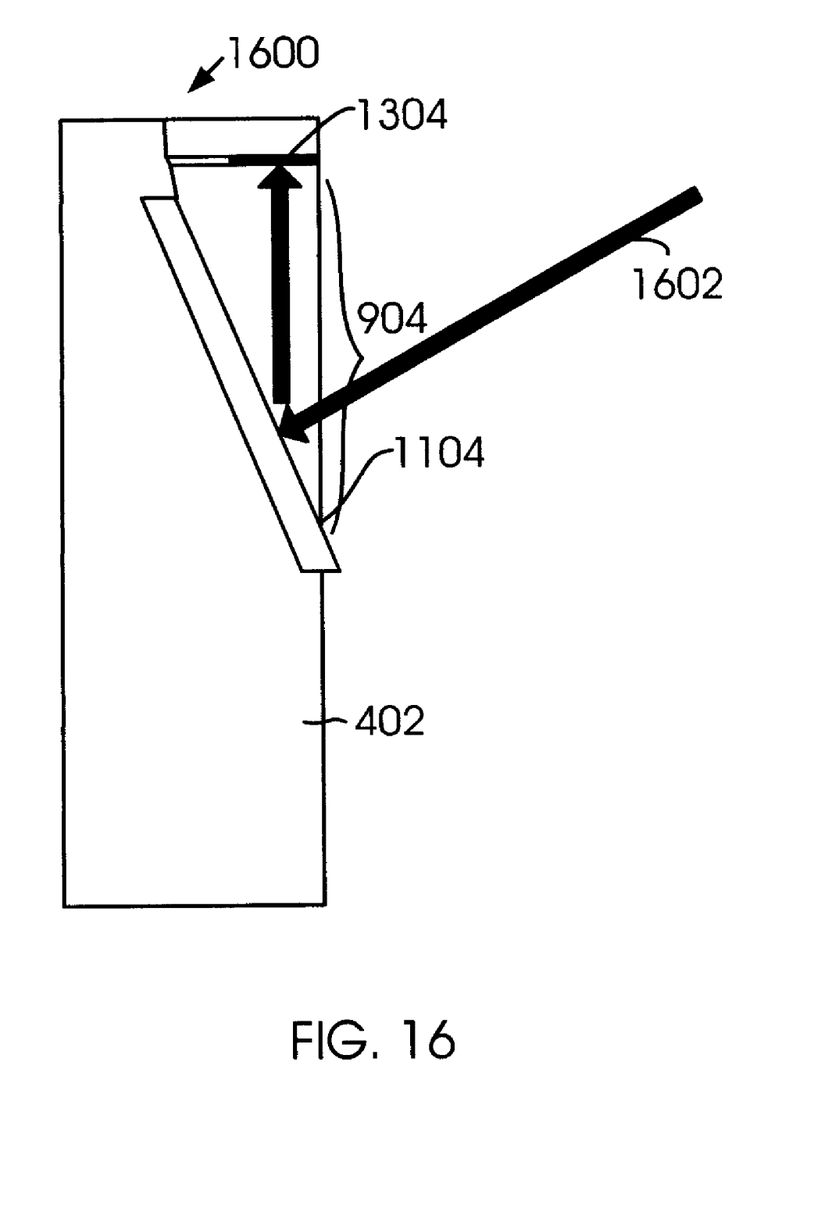
FIG. 16 illustrates a side view of a configuration for irradiating a sample with a laser using the sample of FIG. 14.

In FIG. 16, the laser beam 1602 is generated according to well-known techniques to irradiate a portion of the sample 1304. The laser beam 1602 is reflected by the particle beam channel coating 1104 in the particle beam channel 904 adjacent to the inner side of the sample 1304. The particle beam channel coating 1104 may be, for example, silver or another suitable material for reflecting the laser beam 1602. Other materials may be used for the particle beam channel coating 1104 to practice other embodiments within the scope of the appended claims.

In FIG. 16, the laser beam 1602 is generated according to well-known techniques to irradiate a portion of the sample 1304. The laser beam 1602 is reflected by the particle beam channel coating 1104 in the particle beam channel 904 to the inner side of the sample 1304. The particle beam channel coating 1104 may be, for example, silver or another suitable material for reflecting the laser beam 1602. Other materials may be used for the particle beam channel coating 1104 to practice other embodiments within the scope of the appended claims.

In another embodiment, a method of preparing a sample includes steps of:

providing a sample source that includes an area of interest;

forming an outer side of a sample in the sample source adjacent to the area of interest;

forming an inner side of the sample inside the sample source wherein the sample includes at least a portion of the area of interest between the inner side of the sample and the outer side; and forming a particle beam channel inside the sample source for conducting a particle beam to or from the inner side of the sample.

Figure 17:
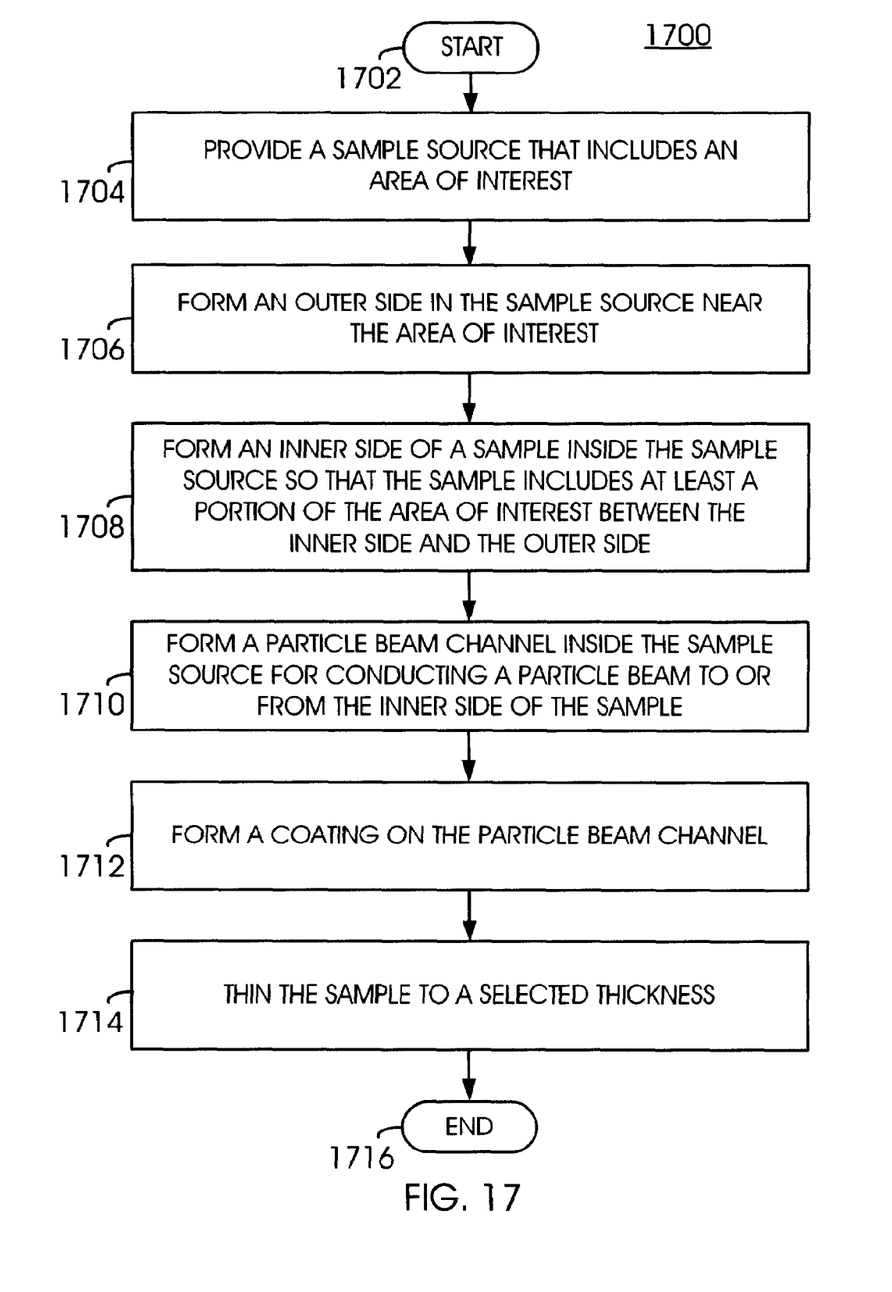
FIG. 17 illustrates a flow chart for a method of preparing the sample of FIG. 14.

FIG. 17 illustrates a flow chart 1700 for a method of preparing the sample of FIG. 14.

Step 1702 is the entry point of the flow chart 1700.

In step 1704, a sample source is provided that includes an area of interest.

In step 1706, an outer side is formed in the sample source near the area of interest, for example, by micro-cleaving the sample source near the area of interest.

In step 1708, material is removed from the sample source as described above to form an inner side of a sample inside the sample source so that the sample includes at least a portion of the area of interest between the inner side and the outer side.

In step 1710, material is removed from the sample source as described above to form a particle beam channel inside the sample source for conducting a particle to or from the inner side of the sample. For example, the particle beam channel may conduct a beam of transmitted electrons from the inner side of the sample and generate secondary electrons, or the particle beam channel may reflect a beam of light and conduct the beam of light to the inner side of the sample.

In step 1712, a coating is formed on the particle beam channel. For example, the coating may be a material such as platinum or gold having a high atomic number for generating secondary electrons from a beam of transmitted electrons received from the sample. In other embodiments, the coating may be a reflective material such as silver for reflecting a laser beam to the sample.

In some embodiments, the particle beam may be a beam of photons, such as X-rays, ultraviolet radiation, infrared radiation, or visible light. In additional embodiments, the particle beam may be a beam of neutrons, protons, or other energetic particles to practice various embodiments within the scope of the appended claims.

Also, the particle beam direction may be reversed from that used in typical scanning electron microscopy, that is, the particle beam may be directed toward the inner side of the sample. For example, a laser beam may be reflected from the particle beam channel to the inner side of the sample to practice various embodiments within the scope of the appended claims.

In step 1714, the sample is thinned to a selected thickness, for example, to pass a beam of transmitted electrons through the area of interest.

Step 1716 is the exit point of the flow chart 1700.

Figure 18:
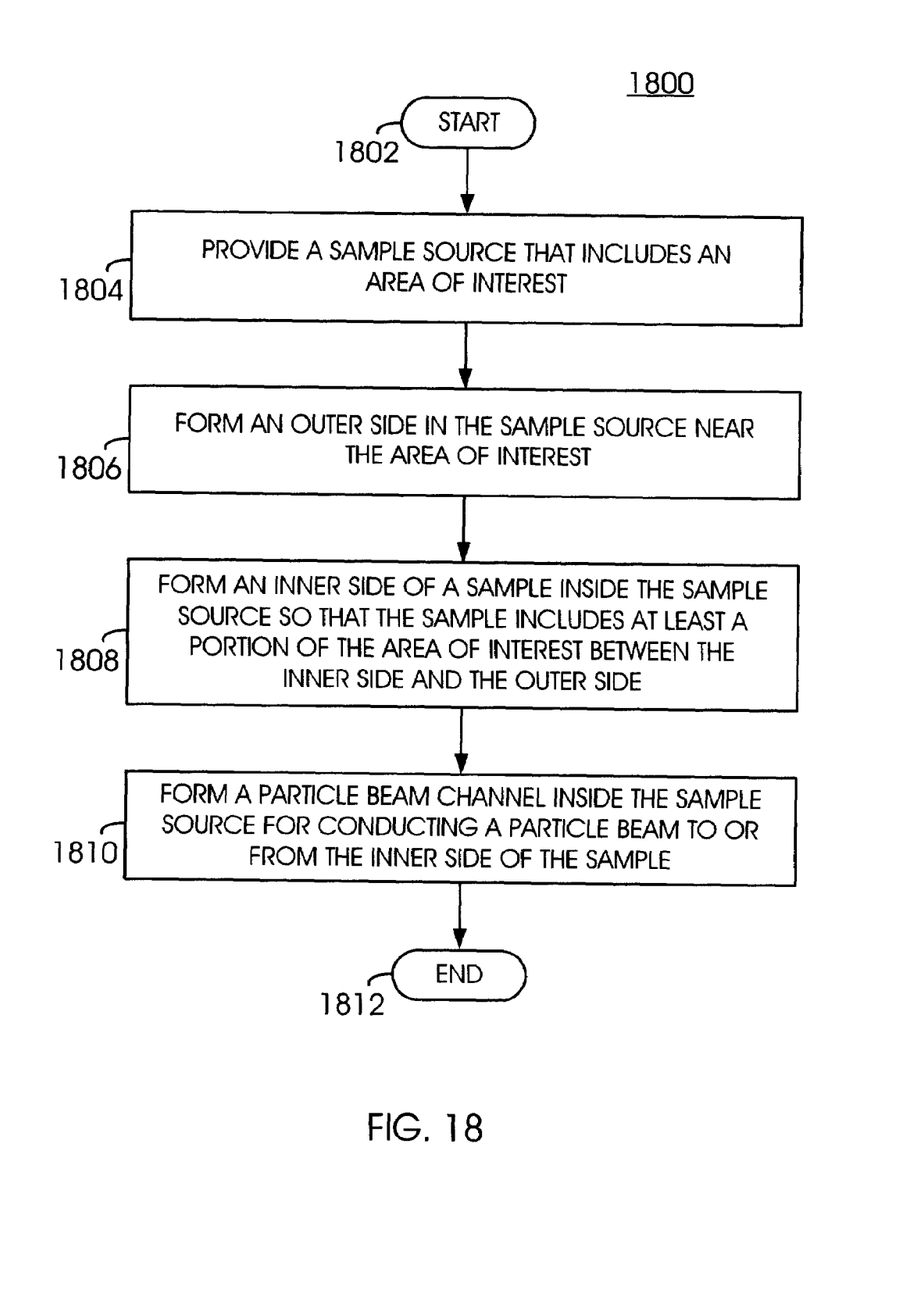
FIG. 18 illustrates a flow chart that summarizes the flow chart of FIG. 17.

FIG. 18 illustrates a flow chart 1800 that summarizes the flow chart of FIG. 17.

Step 1802 is the entry point of the flow chart 1800.

In step 1804, a sample source is provided that includes an area of interest.

In step 1806, an outer side is formed in the sample source.

In step 1808, an inner side of the sample is formed in the sample source so that the sample includes at least a portion of the area of interest between the inner side of the sample and the outer side.

In step 1810, a particle beam channel is formed in the sample source for conducting a particle beam to or from the inner side of the sample.

Step 1812 is the exit point of the flow chart 1800.

As may be appreciated from the above, a sample may be integrated into the sample source with a secondary electron generator for use with a standard in-chamber secondary electron detector, advantageously avoiding the need for an additional secondary electron detector. The sample source may be trimmed to a desired size independently from the size of the sample so that the sample may be handled using ordinary tools, such as wafer handling tools. Further, the sample source may be placed inside a test chamber to prepare the sample inside the test chamber, advantageously avoiding the need to transport the sample into the test chamber from a different environment and possible contamination or other damage to the sample that may occur when the sample is transported.

Although the flowchart descriptions above are described and shown with reference to specific steps performed in a specific order, these steps may be combined, sub-divided, or reordered without departing from the scope of the claims. Unless specifically indicated, the order and grouping of steps is not a limitation of other embodiments that may lie within the scope of the claims.

The specific embodiments and applications thereof described above are for illustrative purposes only and do not preclude modifications and variations that may be made within the scope of the following claims.

What is claimed is:

1. A method comprising steps of:

providing a sample source that includes an area of interest;

forming an outer side of a sample in the sample source adjacent to the area of interest;

forming an inner side of the sample inside the sample source, the sample including at least a portion of the area of interest between the inner side of the sample and the outer side;

forming a particle beam channel inside the sample source for conducting a particle beam to or from the inner side of the sample; and forming a coating on the particle beam channel for one of generating a beam of secondary electrons and reflecting the particle beam.

2. The method of claim 1 further comprising forming the coating comprising one of platinum, silver, and gold.

3. The method of claim 1 further comprising including a portion of a semiconductor wafer in the sample source.

4. The method of claim 1 further comprising including in the sample one of a polysilicon gate of a transistor, a via, an oxide layer, and a polysilicon layer.

5. The method of claim 1 further comprising forming the particle beam channel to conduct a beam comprising electrons or photons.

6. The method of claim 1 further comprising forming the outer side from zero to about 20 microns from the area of interest.

7. The method of claim 1 further comprising forming the particle beam channel including an angular surface, the angular surface formed at an acute angle adjacent to the inner side.

8. An apparatus comprising:
   a sample source that includes an area of interest; an outer side of a sample formed in the sample source adjacent to the area of interest;
   an inner side of the sample formed inside the sample source, the sample including at least a portion of the area of interest between the inner side of the sample and the outer side;
   a particle beam channel formed inside the sample source for conducting a particle beam to or from the inner side of the sample; and
   a coating formed on the particle beam channel for one of generating a beam of secondary electrons and reflecting the particle beam.

9. The sample of claim 8, the coating comprising one of platinum, silver, and gold.

10. The sample of claim 8, the sample source comprising a portion of a semiconductor wafer.

11. The sample of claim 8, the sample comprising one of a polysilicon gate, a via, an oxide layer, and a polysilicon layer.

12. The sample of claim 8, the outer side formed from zero to about 20 microns from the area of interest.

13. The sample of claim 8, the particle beam channel formed to conduct a beam comprising electrons or photons.

14. The apparatus of claim 8, the particle beam channel comprising an angular surface, the angular surface formed at an acute angle adjacent to the inner side.

\* \* \* \* \*